(12) United States Patent
Utschig et al.

(10) Patent No.: US 7,696,722 B2
(45) Date of Patent: Apr. 13, 2010

(54) BATTERY POWERED X-RAY DETECTOR POWER SYSTEM AND METHOD

(75) Inventors: Michael John Utschig, Wauwatosa, WI (US); Jacob Robert Bauer, Menomonee Falls, WI (US); Fred Kleytman, Waukesha, WI (US); Donald Earl Castleberry, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 389 days.

(21) Appl. No.: 11/731,326

(22) Filed: Mar. 30, 2007

(65) Prior Publication Data

US 2008/0240358 A1 Oct. 2, 2008

(51) Int. Cl.
*H01M 10/46* (2006.01)

(52) U.S. Cl. .................................. 320/114

(58) Field of Classification Search .............. 320/107, 320/108, 109, 114, 115, 116; 250/270.09
See application file for complete search history.

(56) References Cited

U.S. PATENT DOCUMENTS 7,495,226 B2 * 2/2009 Jadrich et al. .......... 250/370.09

* cited by examiner

*Primary Examiner*—Edward Tso
(74) *Attorney, Agent, or Firm*—Fletcher Yoder

(57) ABSTRACT

A power system and method for supplying power to a wireless X-ray detector utilizes a detachable handle for a wireless X-ray detector. The handle carries a battery which, when the detachable handle is coupled to a wireless X-ray detector, provides the wireless X-ray detector with a mobile supply of power. A detachable handle charging station may recharge a plurality of detachable handles, providing a swappable supply of power for a wireless X-ray detector. Charging stations for such handles, or for entire detectors are also disclosed.

19 Claims, 4 Drawing Sheets

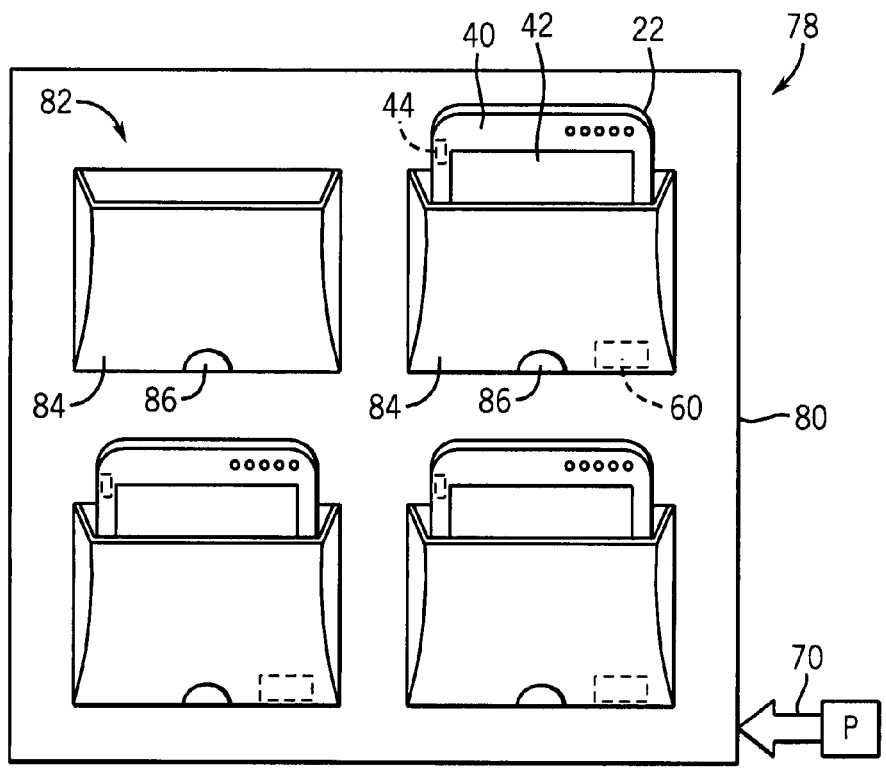
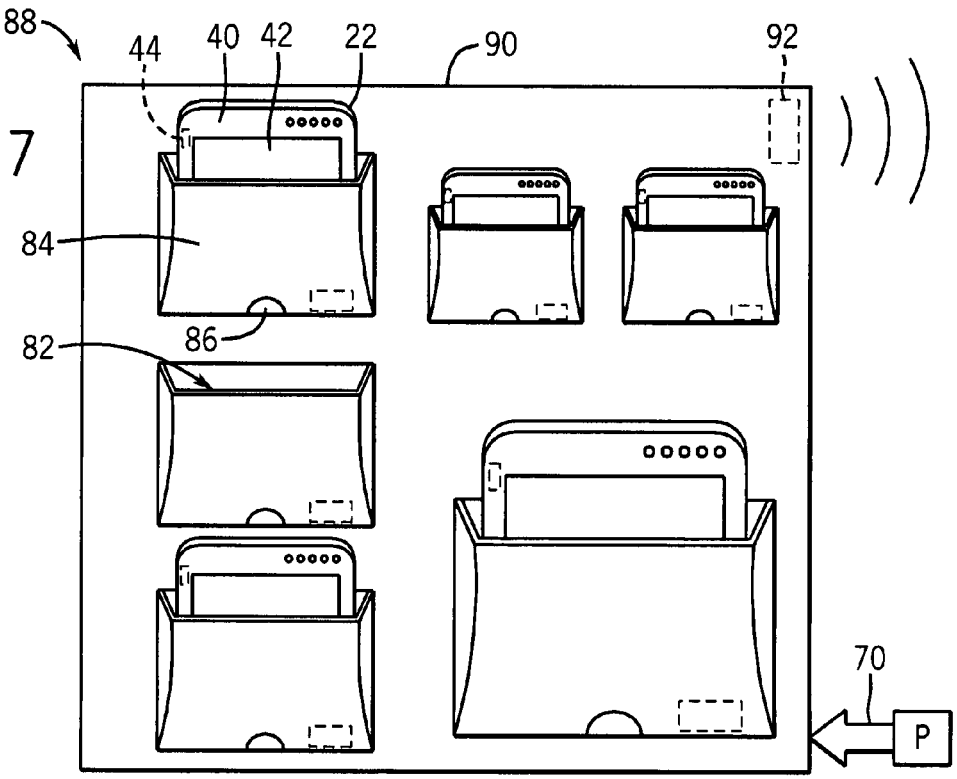

BATTERY POWERED X-RAY DETECTOR POWER SYSTEM AND METHOD

BACKGROUND

The invention relates generally to supplying power to a wireless digital imaging detector, and more particularly, to supplying power to a wireless X-ray detector.

In medical diagnostic applications, digital X-ray imaging systems offer exceptional versatility and rapid reconstruction of radiographic images. A digital X-ray imaging system consists of at least a radiation source, a detector, and an image data processor and display. Radiation from a source is directed toward a subject, typically a patient, and a portion of the radiation passes through the subject and impacts a detector, which transforms the radiation into useful image data. After receiving the image data, an image data processor translates the data into a radiographic image for display.

As digital X-ray imaging systems have become increasingly widespread, digital X-ray detectors have become more portable for even greater versatility. Rather than remaining fixed against a table or wall, some digital X-ray detectors may be moved freely, remaining tethered only to a host computer and power supply. Such a configuration, however, may prove limiting in many applications. The tether may not allow the wireless detector to reach or turn as desired. Also, the tether may become tangled, and may present a tripping hazard to those in the vicinity. Moreover, recoiling the tether while connected to the detector may prove cumbersome to medical personnel. To overcome such limitations, attempts have been made to allow for wireless operation of digital X-ray detectors.

Though a wireless X-ray detector may offer greater mobility, its emancipation requires a power system as mobile as the wireless X-ray detector itself. Such a power system must further endure a strenuous medical environment in which a wireless X-ray detector may be deployed, as well as accommodate wireless X-ray detectors throughout a range of varying applications. Additionally, it may be desirable to allow the wireless X-ray detector to remain in position while a depleted power supply is replaced.

BRIEF DESCRIPTION

The invention features a power system and method for a wireless X-ray detector designed to address such needs. In accordance with one aspect of the present invention, a detachable handle for a wireless X-ray detector carries a battery which, when the detachable handle is coupled to a wireless X-ray detector, provides the wireless X-ray detector with a mobile supply of power. A detachable handle charging station may recharge a plurality of detachable handles, providing a swappable supply of power for a wireless X-ray detector.

In accordance with another aspect of the present invention, a non-communicative wireless X-ray detector charging station recharges a plurality of wireless X-ray detectors, each carrying a rechargeable battery. The wall-mountable charging station remains completely independent of all data acquisition and processing activity. Furthermore, the charging station does not communicate with any digital X-ray imaging system components, simplifying the manufacture and design of the charging station.

In accordance with yet another aspect of the present invention, a wireless X-ray detector charging station recharges a plurality of wireless X-ray detectors of varying shapes and sizes, each carrying a rechargeable battery. The charging station may additionally comprise a wireless transceiver and additional data processing and detector monitoring circuitry, which may allow, for example, remote monitoring of the location and charge level of each wireless X-ray detector.

DRAWINGS

These and other features, aspects, and advantages of the present invention will become better understood when the following detailed description is read with reference to the accompanying drawings in which like characters represent like parts throughout the drawings, wherein:

FIG. 6 illustrates an exemplary non-communicative charging station for charging a plurality of wireless X-ray detectors in accordance with one embodiment of the present invention; and FIG. 7 illustrates an exemplary charging station for charging a plurality of wireless X-ray detectors of varying shapes and sizes in accordance with one embodiment of the present invention.

DETAILED DESCRIPTION

Figure 1:
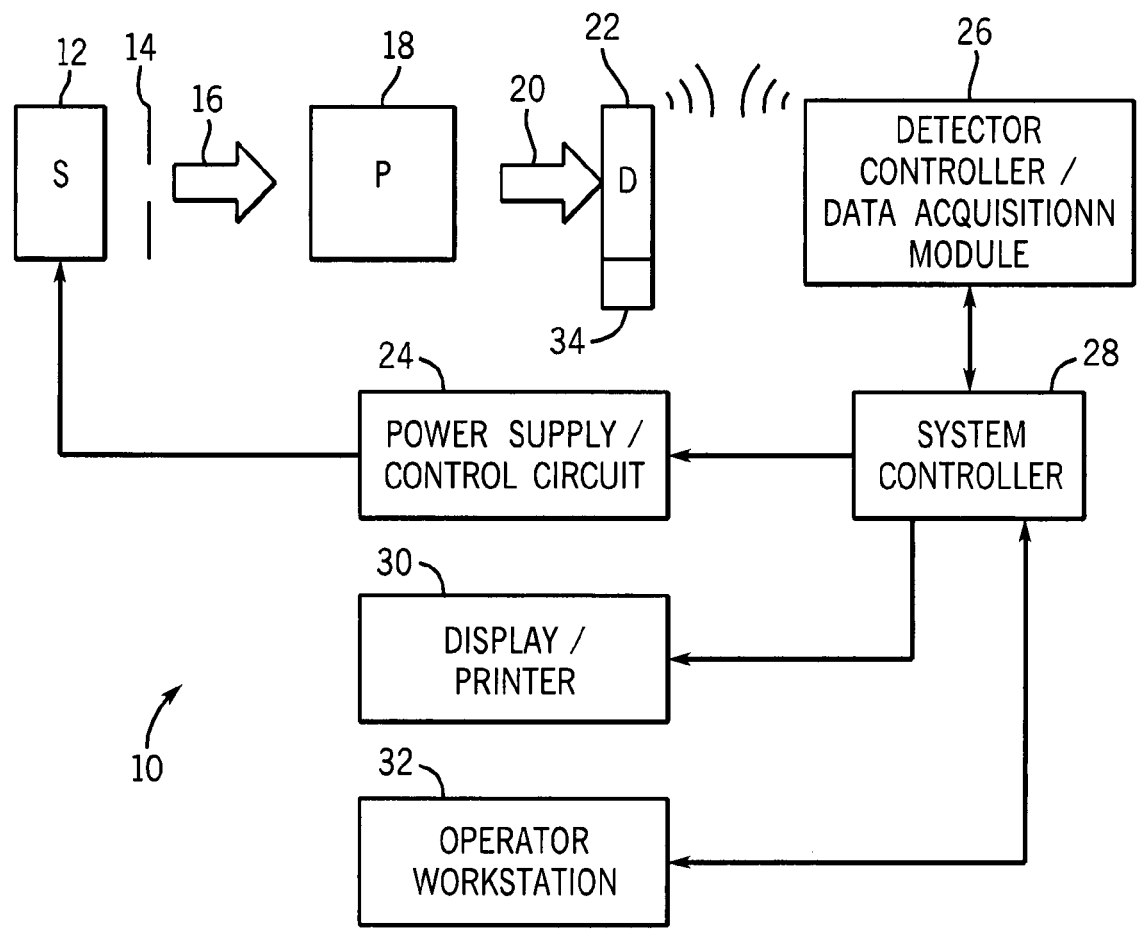
FIG. 1 is a diagrammatical representation of an exemplary digital X-ray imaging system employing a wireless detector in accordance with one embodiment of the present invention.

FIG. 1 illustrates a block diagram of an exemplary digital wireless X-ray imaging system 10. In accordance with an embodiment of the present invention, imaging system 10 is a digital X-ray imaging system configured both to acquire original image data and to process the image data for display, with the digital X-ray detector freely detached from the remaining system components. Imaging system 10 includes a source of X-ray radiation 12 adjacent to a collimator 14. Collimator 14 passes a stream of radiation 16 into a region wherein a subject, such as a human patient 18, is positioned. A portion of the radiation 20 passes through or around the subject and impacts the adjacent wireless X-ray detector 22.

Source 12 may be controlled by a power supply and control circuit 24 which supplies both power and control signals for examination sequences. To obtain the image data resulting from radiation impacting the wireless X-ray detector 22, a detector controller and data acquisition module 26 receives image data signals from wireless X-ray detector 22 and transmits control signals to wireless X-ray detector 22. Alternatively, the detector controller may reside within the wireless X-ray detector 22 and separate from the data acquisition module, in which case wireless communication takes place between the wireless X-ray detector 22 and the data acquisition module. Power supply and control circuit 24 and detector controller and data acquisition module 26 are both responsive to signals from a system controller 28. In general, system controller 28 commands operation of the imaging system to execute examination protocols and to process acquired image data. The system controller 28 may also include signal processing circuitry based on a general purpose or application-specific computer, associated memory circuitry, configuration parameters and image data, and so forth. System controller 28 links to at least one output device, such as a display or printer 30. One or more operator workstations 32 may be additionally joined in the system for outputting system parameters, requesting examinations, viewing images, and so forth.

In the embodiment illustrated in FIG. 1 a portable power supply 34 is attached to the wireless X-ray detector 22. The portable power supply 34 may function as the exclusive power supply of the wireless X-ray detector, but may also serve as a power pack designed to provide additional power if a battery carried by the wireless X-ray detector 22 becomes depleted during a medical procedure. If desired, the wireless X-ray detector 22 may remain in position while a depleted detachable handle power supply 34 is detached and replaced with a more fully charged detachable handle power supply 34. Moreover, the portable power supply 34 may also serve to allow free movement of the detector when the detector is not otherwise powered by a conventional power cord or cable (not shown).

Figure 2:
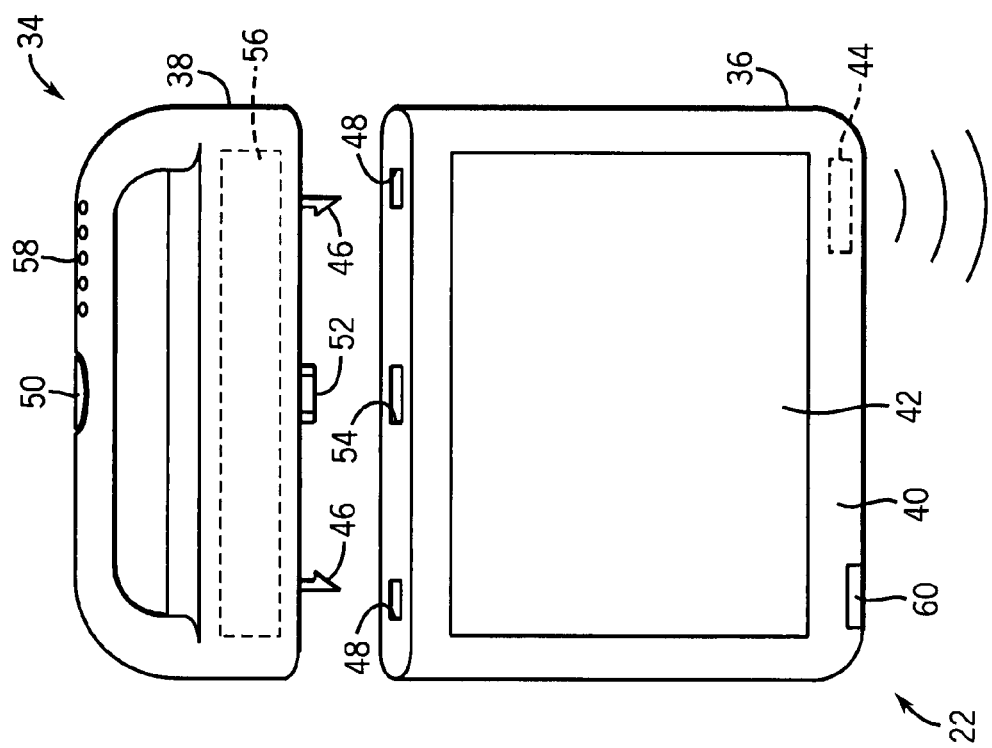
FIG. 2 illustrates an exemplary detachable handle portable power supply detached from a wireless X-ray detector in accordance with one embodiment of the present invention.

FIG. 2 illustrates an exemplary portable detachable handle power supply 34 as viewed when detached from a wireless X-ray detector 22. Wireless X-ray detector 22 comprises an outer casing 36, which resists moisture and prevents damage to internal components during routine handling. Detachable handle outer casing 38 similarly protects the detachable handle power supply 34 from moisture and internal damage during routine handling. Outer casing 38 may also include a removable hatch for access to a battery or to internal circuitry, around which a seal may prevent moisture from entering when the removable hatch is closed. The handle is depicted in FIG. 2 with a thru-hole type feature, but it may also employ any of a variety of features to facilitate handling such as a depression, a protrusion, a secondary high friction material, or geometric features such as ribs, etc.

The casing 40 of wireless X-ray detector 22 surrounds the X-ray detector imager assembly (not depicted in FIG. 2). The X-ray detector imager assembly includes a scintillator surface, which converts X-ray radiation into lower energy photons for subsequent detection by an underlying array of photodiodes and thin film transistors. The scintillator surface may comprise a variety of layers, including a reflective outer layer and moisture resistant sublayers. The casing 40 typically contains a region or window 42 that is relatively transparent to X-rays to maximize X-ray capture and which is often visually or tactilely distinct from the casing 40 to enable correct placement of the detector behind the patient.

Detector casing 40 may further contain components which control and at least partially process data generated by the X-ray detector imager assembly, which may include, for example, a detector controller, detector power control circuitry, memory circuitry, and a wireless transceiver 44. Used to communicate wirelessly with the detector controller and data acquisition module 26 (illustrated in FIG. 1), the wireless transceiver 44 may employ any suitable wireless communication protocol. Depending on the desired range of the wireless signal, wireless transceiver 44 may permit significantly remote use of the wireless X-ray detector 22.

Any effective means may be used to physically attach the detachable handle power supply 34 to wireless X-ray detector 22, including, for example, interconnecting locking hooks 46 with locking hook receptacles 48. Locking hooks 46 may engage locking hook receptacles 48 with assistance from a spring-loaded or motorized mechanism (not depicted) drawing the locking hooks 46 toward each other. A locking hook release button 50 releases locking hooks 46 from locking hook receptacles 48 when depressed, as locking hooks 46 spread apart against the force of the spring-loaded mechanism or change position due to the motorized mechanism. To avoid accidental release, the locking hook release button 50 may be configured not to release locking hooks 46 from locking hook receptacles 48 unless an optional additional button is simultaneously pressed or until after the locking hook release button 50 has been depressed for a desired time.

The detachable handle power supply 34 of FIG. 2 provides power to the wireless X-ray detector 22 by operably joining a male electrical coupling structure 52 on the handle to a female electrical coupling structure 54 on the detector. The electrical coupling structures 52 and 54 may comprise pins and mating contacts or a standard electrical plug and receptacle arrangement for conductively transferring power, but may alternatively comprise an induction device which induces a charge in a receiving device to inductively transfer power. Moreover, the male and female structures may appear in reverse, or both male and female coupling structures may appear on each of the detachable handle power supply 34 and wireless X-ray detector 22. The electrical coupling structures 52 and 54 may additionally serve to stabilize the handle when attached. For greater stability, stabilization pins may also be employed.

Wireless X-ray detector 22 consumes power from a battery 56 carried by the detachable handle power supply 34. The battery 56 may reside within the detachable handle in any desired shape, behind a removable hatch, or within a recess external to the detachable handle such that the battery 56 may snap into place and resemble the external surface of the detachable handle. Depending on the desired application and configuration, the battery 56 may be replaceable or rechargeable. The energy remaining in battery 56 may be displayed on a power level monitor 58 consisting of an LED or LCD panel. When the battery 56 nears depletion, power level monitor 58 may flash or emit an audible warning sound to indicate the need to replace or recharge the battery 56.

Optionally, the wireless X-ray detector 22 may also carry a battery (not depicted in FIG. 2), in which case the battery 56 carried by the detachable handle power supply 34 may preferably discharge before the battery carried by the wireless X-ray detector 22. A battery carried by the wireless X-ray detector may reside within the detector in any desired shape, behind a removable hatch, or within a recess external to the detector such that the battery may snap into place and resemble the external surface of the wireless X-ray detector 22. When the wireless X-ray detector 22 carries a battery, a power level monitor on the wireless X-ray detector may provide an indication of the charge status of that battery on an LED or LCD panel (not depicted in FIG. 2). Such a battery may be separately recharged via an external electrical coupling device 60 along the outer edge 40 of the wireless X-ray detector 22, as discussed in greater detail below.

Figure 3:
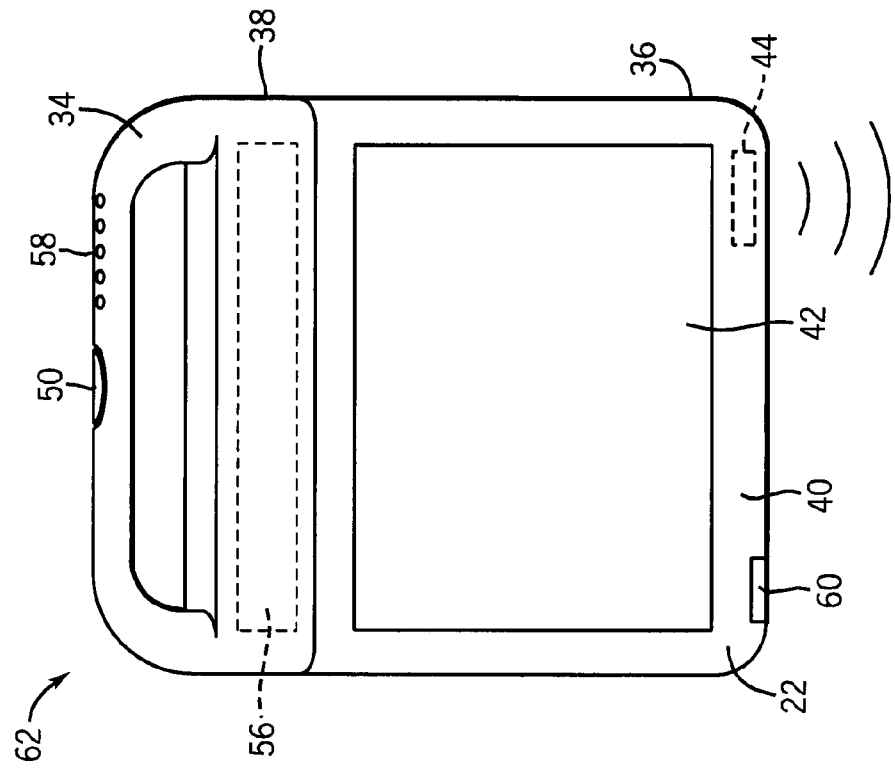
FIG. 3 illustrates an exemplary detachable handle portable power supply attached to a wireless X-ray detector in accordance with one embodiment of the present invention.

FIG. 3 illustrates an exemplary combined wireless X-ray detector and detachable handle power supply 62 in accordance with one embodiment of the present invention. When combined, the detachable handle power supply 34 provides power from battery 56 to the wireless X-ray detector 22.

Figure 4:
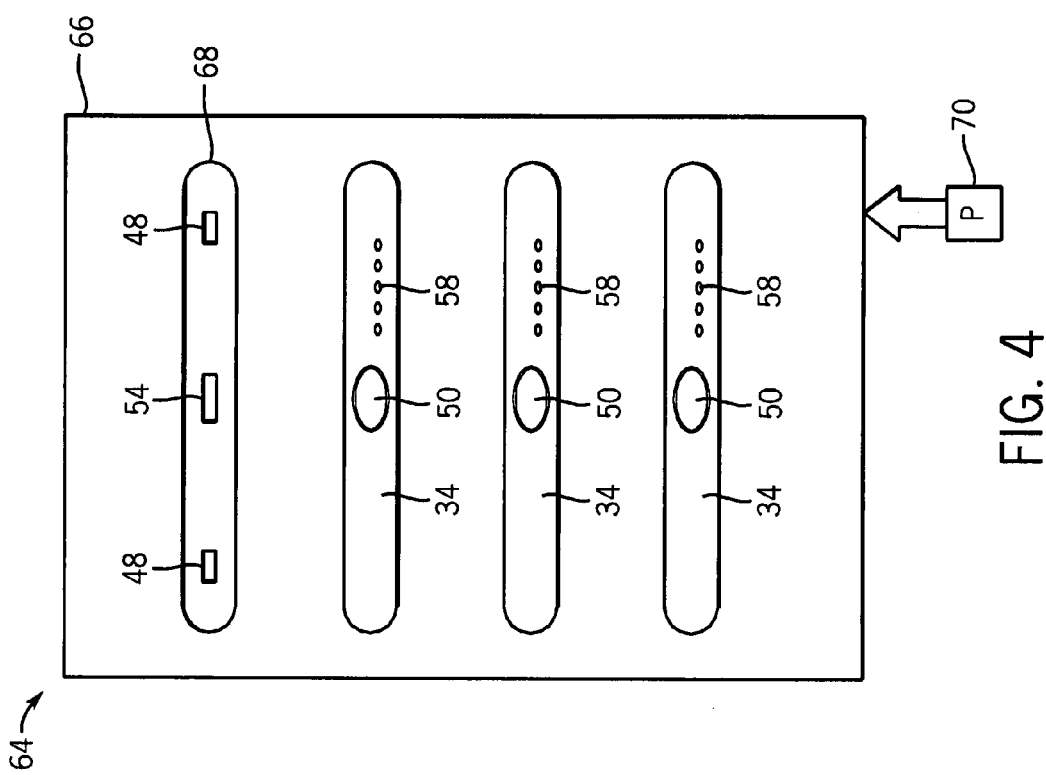
FIG. 4 illustrates an exemplary detachable handle charging station for charging detachable handle portable power supplies for a wireless X-ray detector according to one embodiment of the present invention.

FIG. 4 illustrates an exemplary detachable handle charging station 64 for horizontally charging a plurality of detachable handle power supplies 34. A wall-mountable base 66 includes on its face a plurality of detachable handle charging sites 68, each of which comprises locking hook receptacles 48 and a female electrical coupling structure 54. Angled upwardly, each detachable handle charging site 68 provides a comfortable angle at which to engage and disengage each detachable handle power supply 34.

A standard wall power outlet 70 provides power to the wall-mountable base 66, which converts the alternating current power into direct current power, distributing the power to each detachable handle charging site 68. To begin charging, a detachable handle power supply 34 attaches to a detachable handle charging site 68 in the same manner as to a wireless X-ray detector 22, interconnecting locking hooks 46 with locking hook receptacles 48 and operably joining male electrical coupling structure 52 with female electrical coupling structure 54. The electrical coupling structures 52 and 54 may comprise pins and mating contacts or a standard electrical plug and receptacle arrangement for conductively transferring power, but may alternatively comprise an induction device which induces a charge in a receiving device to inductively transfer power.

Once attached, a power management circuit within the detachable handle power supply 34 regulates the charging of the battery 56. The power level monitor 58 provides an indication of the charge status, and may provide a visual or auditory signal upon charge completion. Alternatively, each detachable handle charging site 68 may additionally provide an indication of the charge status of a charging detachable handle power supply 34.

Figure 5:
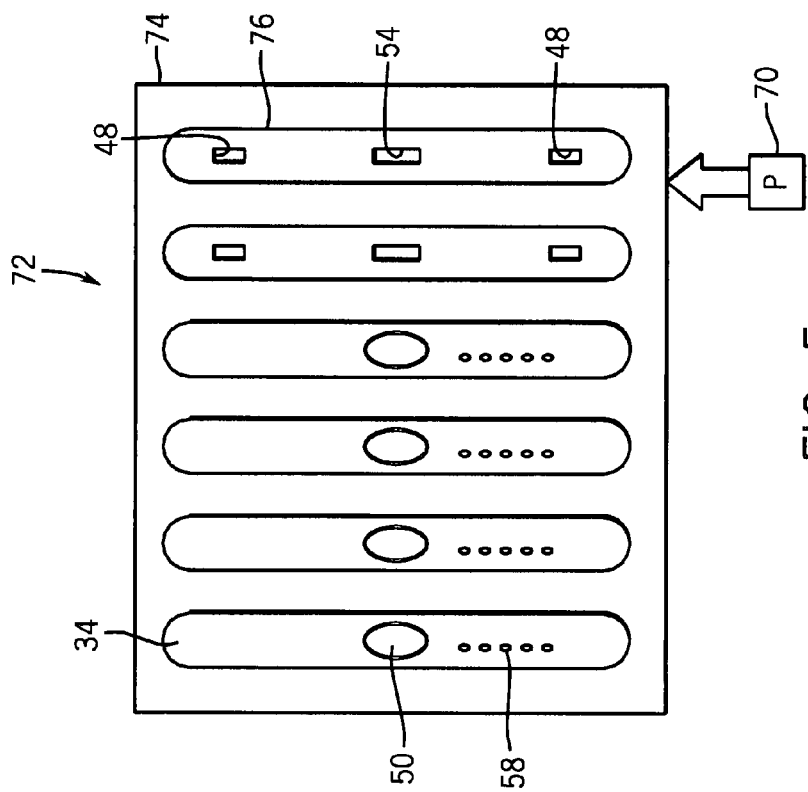
FIG. 5 illustrates another exemplary detachable handle charging station for charging detachable handle portable power supplies for a wireless X-ray detector according to one embodiment of the present invention.

FIG. 5 illustrates an exemplary embodiment of a detachable handle charging station 72 for vertically charging a plurality of detachable handle power supplies 34. Wall-mountable base 74 includes on its face a plurality of vertically-oriented detachable handle charging sites 76. Detachable handle charging station 72 functions in a fashion similar to that described with respect to the charging station 64 of FIG. 4, discussed above.

FIG. 6 illustrates an exemplary non-communicative charging station 78 for charging a plurality of wireless X-ray detectors 22, each carrying a rechargeable battery. In the embodiment depicted by FIG. 6, charging station 78 remains completely independent of all data acquisition and processing activity and does not communicate with any digital X-ray imaging system components, simplifying the manufacture and design of the charging station. A wall-mountable base 80 includes on its face a plurality of wireless X-ray detector charging sites 82, each of which comprises a detector holder 84 and an optional release button 86. A standard wall power outlet 70 provides power to the wall-mountable base 80, which adapts the alternating current power into direct current power, distributing the power to each wireless X-ray detector charging site 82.

Each charging site 82 includes an electrical coupling structure residing within each detector holder 84. The electrical coupling structure is configured to transfer power to a rechargeable battery carried by a wireless X-ray detector 22 by way of an external electrical coupling device 60 on the wireless X-ray detector 22. The electrical coupling structure of the detector holder 84 and the electrical coupling device 60 may comprise pins and mating contacts or a standard electrical plug and receptacle arrangement for conductively transferring power, or may alternatively comprise an induction device which induces a charge in the receiving device to inductively transfer power.

Once attached to a wireless X-ray detector charging site 82, a power management circuit within the wireless X-ray detector 22 regulates the charging of the battery. A power level monitor on the wireless X-ray detector 22 may provide an indication of the charge status, and may further provide a visual or auditory signal upon charge completion. Alternatively, each charging site 82 may additionally include a power level monitor to provide an indication of the charge status of the battery carried by each wireless X-ray detector 22.

FIG. 7 illustrates an exemplary charging station 88 for charging a plurality of wireless X-ray detectors 22 of varying shapes and sizes, each carrying a rechargeable battery. A wall-mountable base 90 includes on its face a plurality of wireless X-ray detector charging sites 82 of varying sizes, each of which comprises a detector holder 84 of corresponding shape and size and an optional release button 86. A standard wall power outlet 70 provides power to the wall-mountable base 80, which adapts the alternating current power into direct current power, distributing the power to each wireless X-ray detector charging site 82.

As in the embodiment illustrated in FIG. 6, each charging site 82 in the embodiment illustrated in FIG. 7 includes an electrical coupling structure residing within each detector holder 84. The electrical coupling structure is configured to transfer power to a rechargeable battery carried by a wireless X-ray detector 22 by way of an external electrical coupling device 60 on the wireless X-ray detector 22. The electrical coupling structure of the detector holder 84 and the electrical coupling device 60 may comprise pins and mating contacts or a standard electrical plug and receptacle arrangement for conductively transferring power, or may alternatively comprise an induction device which induces a charge in the receiving device to inductively transfer power.

Once attached to a wireless X-ray detector charging site 82, a power management circuit within the wireless X-ray detector 22 regulates the charging of the battery. A power level monitor on the wireless X-ray detector 22 may provide an indication of the charge status, and may further provide a visual or auditory signal upon charge completion. Alternatively, each charging site 82 may additionally include a power level monitor to provide an indication of the charge status of the battery carried by each wireless X-ray detector 22.

Charging station 88, as illustrated by FIG. 7, may further comprise a wireless transceiver 92, as well as additional data processing and detector monitoring circuitry within base structure 90. The additional communicative ability conferred by wireless transceiver 92 could allow the charging station 88, for example, to remotely monitor the location and charge level of each wireless X-ray detector 22 or to receive and retransmit signals from a wireless transceiver 44 on each wireless X-ray detector 22 to a remote base station.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A power system for a battery powered X-ray detector, comprising:
    a battery;
    a detachable handle configured to carry the battery;
    a mechanical coupling structure configured to attach the detachable handle to a battery powered X-ray detector;
    an electrical coupling structure configured to transfer power from the battery to the battery powered X-ray detector; and
    a battery charge level indicator.
2. The power system of claim 1, wherein the electrical coupling structure is configured to conductively transfer power from the battery to the battery powered X-ray detector.

3. The power system of claim 1, wherein the electrical coupling structure is configured to inductively transfer power from the battery to the battery powered X-ray detector.

4. The power system of claim 1, wherein the battery is a replaceable battery.

5. The power system of claim 1, wherein the battery is a rechargeable battery.

6. The power system of claim 5, wherein the electrical coupling structure is also configured to transfer power from a charging device to the battery.

7. The power system of claim 6, further comprising a detachable handle charging station configured to recharge the battery while the battery is being carried by the detachable handle.

8. A charging station for recharging a battery carried by a detachable handle configured to power a battery powered X-ray detector, comprising:
   a power adapter configured to adapt power from an external power source to power suitable for charging a rechargeable battery;
   a detachable handle charging site configured to receive a supply of power suitable for charging a rechargeable battery from the power adapter; the site including a mechanical coupling structure configured to attach a detachable handle to the detachable handle charging site, and an electrical coupling structure configured to transfer power from the supply of power suitable for charging a rechargeable battery to the detachable handle; and
   a battery charge level indicator.

9. The charging station of claim 8, further comprising a plurality of detachable handle charging sites.

10. The charging station of claim 8, wherein the electrical coupling structure is configured to conductively transfer power from the supply suitable for charging a rechargeable battery to the detachable handle.

11. The charging station of claim 8, wherein the electrical coupling structure is configured to inductively transfer power from the supply suitable for charging a rechargeable battery to the detachable handle.

12. A charging station for recharging rechargeable batteries for battery powered X-ray detectors, comprising:
   a power adapter configured to adapt power from an external power supply to power suitable for charging rechargeable batteries; and
   a plurality of battery powered X-ray detector detachable handle charging sites configured to receive a supply of power from the power adapter suitable for charging rechargeable batteries, each site including a mechanical coupling structure configured to attach a battery powered X-ray detector detachable handle to the battery powered X-ray detector detachable handle charging site, and an electrical coupling structure configured to transfer power from the supply of power suitable for charging rechargeable batteries of different shapes and sizes.

13. The charging station of claim 12, wherein the electrical coupling structure is configured to conductively transfer power suitable for charging a rechargeable battery to the battery carried by the battery powered X-ray detector detachable handle.

14. The charging station of claim 12, wherein the electrical coupling structure is configured to inductively transfer power suitable for charging a rechargeable battery to the battery carried by the battery powered X-ray detector detachable handle.

15. A charging station for recharging a rechargeable battery carried by a battery powered X-ray detector, comprising:
   a power adapter configured to adapt power from an external power supply to power suitable for charging a rechargeable battery; and
   at least one battery powered X-ray detector charging site configured to charge battery powered X-ray detectors, the battery powered X-ray detector charging site including a mechanical coupling structure configured to attach a battery powered X-ray detector to the battery powered X-ray detector charging site, and an electrical coupling structure configured to transfer power from a power supply to a battery carried by the battery powered X-ray detector.

16. The charging station of claim 15, wherein each battery powered X-ray detector charging site further comprises a data transfer facilitation structure configured to download data from the battery powered X-ray detector to the charging station and wherein the charging station may communicate with a remote host.

17. The charging station of claim 15, wherein the electrical coupling structure is configured to conductively transfer power from the power supply to the battery carried by the battery powered X-ray detector.

18. The charging station of claim 15, wherein the electrical coupling structure is configured to inductively transfer power from the power supply to the battery carried by the battery powered X-ray detector.

19. The charging station of claim 15, further comprising a plurality of battery powered X-ray detector charging sites configured to charge battery powered X-ray detectors of different shapes and sizes.

* * * * *